(12) United States Patent
Sakaguchi et al.

(10) Patent No.: US 8,950,577 B2
(45) Date of Patent: Feb. 10, 2015

(54) IMPLANT FIXTURE STORAGE CASE AND IMPLANT FIXTURE STORAGE CASE SET

(71) Applicant: GC Corporation, Tokyo (JP)

(72) Inventors: Yoshihiro Sakaguchi, Tokyo (JP); Kinya Nihei, Tokyo (JP); Seiko Muraoka, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 14/254,182

(22) Filed: Apr. 16, 2014

(65) Prior Publication Data
US 2014/0311932 A1   Oct. 23, 2014

(30) Foreign Application Priority Data

Apr. 17, 2013  (JP) ................................. 2013-086592

(51) Int. Cl.
*A61B 19/02*  (2006.01)
*A61C 19/02*  (2006.01)

(52) U.S. Cl.
CPC ...................................... *A61C 19/02* (2013.01)
USPC ...................................... 206/63.5; 206/459.5

(58) Field of Classification Search
USPC ............. 206/63.5, 438, 459.5, 368, 776, 782; 433/8, 9, 172, 173
See application file for complete search history.

(56) References Cited

U.S. PATENT DOCUMENTS

| | | | | |
|---|---|---|---|---|
| 5,887,707 A * | 3/1999 | Anascavage et al. | ........ | 206/63.5 |
| 5,967,305 A * | 10/1999 | Blonder et al. | ............. | 206/63.5 |
| 5,979,643 A * | 11/1999 | Blonder et al. | ............. | 206/63.5 |
| 6,086,371 A * | 7/2000 | Bassett et al. | ................. | 433/173 |
| 8,083,054 B2 | 12/2011 | Nihei et al. | | |
| 8,251,076 B2 * | 8/2012 | Souza | ........................... | 132/309 |
| 2003/0196922 A1* | 10/2003 | Reaux | ........................... | 206/370 |
| 2003/0221977 A1* | 12/2003 | Kumar et al. | ................ | 206/63.5 |
| 2004/0124105 A1* | 7/2004 | Seiler et al. | .................... | 206/363 |
| 2008/0283432 A1 | 11/2008 | Takahashi et al. | | |
| 2009/0266728 A1* | 10/2009 | Turner et al. | .................. | 206/363 |

FOREIGN PATENT DOCUMENTS

| | | |
|---|---|---|
| JP | 2008-284145 A | 11/2008 |
| JP | 2011-218039 A | 11/2011 |
| WO | 99/65416 A1 | 12/1999 |

* cited by examiner

*Primary Examiner* — Jacob K Ackun
(74) *Attorney, Agent, or Firm* — Ladas & Parry LLP (57) ABSTRACT

Provided is an implant fixture storage case capable to prevent mistake in combination. The implant fixture storage case comprises an implant fixture holding member (20) for holding an implant fixture and which has a length based on the implant fixture to be held, and a storage main body (10) on which a value related to the length of the implant fixture is displayed, and which holds the implant fixture holding member thereinside and has at least one part being transparent, and a position display means (12) provided to the storage main body based on a position of an end portion of the implant fixture holding member, wherein the end portion of the implant fixture holding member and the position display means are viewable at the same time.

6 Claims, 8 Drawing Sheets

IMPLANT FIXTURE STORAGE CASE AND IMPLANT FIXTURE STORAGE CASE SET

TECHNICAL FIELD

The present invention relates to an implant fixture storage case that is a case to store a dental implant fixture to be used for dental implant treatment, and an implant fixture storage case set comprising a plurality of implant fixture storage cases.

BACKGROUND ART

Nowadays, as one of dental prosthesis treatments, a technique to embed an implant fixture (sometimes referred to as an artificial tooth root or an implant body) to a jaw bone of a site of defective tooth, and using the implant fixture as a substitute for a natural tooth, to attach an artificial tooth to the implant fixture directly or via another member (for example, an abutment) has been widely used.

The implant fixture as mentioned above is strongly required to be hygienic, judging from its nature, and from this viewpoint, an implant fixture storage case that protects the implant fixture from damage and keeps the implant fixture in a hygienic state is used until just before the implant fixture is used. Patent Document 1 (Japanese Patent Application Laid-Open (JP-A) No. 2008-284145) and Patent Document 2 (Japanese Patent Application Laid-Open (JP-A) No. 2011-218039) each discloses an implant fixture storage case like the above.

In Patent Document 1, as an implant fixture storage case having a high sealing property capable of keeping sterile condition, the case comprising a storage main body made of titanium material and formed in a bottomed cylindrical shape is disclosed. Also, in Patent Document 2, an implant fixture storage case comprising a storage main body made of glass or plastic and formed in a case shape, an implant fixture holding member made of titanium or titanium alloy and having a predetermined shape to hold an implant fixture, and a cap to seal the storage main body is disclosed.

SUMMARY OF THE INVENTION

Problems to be Solved by the Invention

However, in the implant fixture storage case described in Patent Document 1, the storage main body is made of titanium material, thereby having a problem that the titanium material is wasted, considering the fact that the implant fixture storage case is used only once and thrown away.

On the other hand, in the implant fixture storage case described in Patent Document 2, the storage main body is formed of glass, plastic and the like, and the member to hold an implant fixture directly is stored in the storage main body, thereby it is possible to reduce amount of titaniuim material to be used. However, the implant fixture storage case described in Patent Document 2 is configured by a plurality of members combined with one another.

Different kinds of implant fixtures that have different lengths are prepared to be matched for a patient. Therefore, a practitioner such as a dentist decides which implant fixture to use, and based on the decision, the implant fixture is embedded in the jaw bone of the patient.

On the implant fixture storage case, a length of the implant fixture to be stored in the implant fixture storage case is displayed. Normally, the practitioner chooses the implant fixture according to the display and the operation is carried out. Therefore, a provider of the implant fixture must not pair an implant fixture with a case displaying wrong length of the implant fixture that is actually stored. In this view point, in the invention described in Patent Document 2, there is a risk of wrongly pairing the storage main body and a wrong implant fixture holding member. It should be noted that there has been no mistake as above until now, however, if it is possible to apply a means to prevent such a mistake in a convincing way, reliability can be further improved. It is also important to reduce burden of workers to check.

Accordingly, an object of the present invention is to provide an implant fixture storage case capable to prevent mistake in combination and to provide an implant fixture storage case set including a plurality of implant fixture storage cases.

SUMMARY OF INVENTION

Problem to be Solved by Invention

Hereinafter, the present invention will be described. In order to make the description easy to understand, reference numerals in the accompanying drawings are represented in parentheses; however, the present invention is not limited to this.

A first aspect of the present invention is an implant fixture storage case (1) comprising an implant fixture holding member (20) for holding an implant fixture and which has a length based on a length of the implant fixture to be held, and a storage main body (10) on which a value related to the length of the implant fixture is displayed, and which holds the implant fixture thereinside and has at least one part being transparent, and a position display means (12) provided to the storage main body based on an end portion of the implant fixture holding member, wherein the end portion of the implant fixture holding member and the position display means are viewable at the same time.

A second aspect of the present invention is the implant fixture storage case (1) according to the first aspect of the present invention, wherein a site on which the value related to the length of the implant fixture is displayed is also used for the position display means.

A third aspect of the present invention is the implant fixture storage case (1) according to the second aspect of the present invention, wherein the site on which the value related to the length of the implant fixture is displayed is a site sectioned in a rectangle shape, and one side of the rectangle shape functions as the position display means.

A fourth aspect of the present invention is the implant fixture storage case (1) according first aspect of the present invention, wherein the implant fixture holding member (20) is formed in a cylindrical shape having a bottom on one side.

A fifth aspect of the present invention is an implant fixture storage case set (50) comprising a plurality of the implant fixture storage cases (1) according to the first aspect of the present invention.

A sixth aspect of present invention is the implant fixture storage case set (50) according to the fifth aspect of the present invention, wherein the plurality of the implant fixture storage cases (1) have at least two kinds of the implant fixture holding members (20) having different lengths from each other.

Effects of the Invention

According to the present invention, when the implant fixture holding member that has a length based on the implant fixture to be held and the position display means provided to the storage main body are correctly paired, they have a predetermined positional relationship and the relationship is viewable. Therefore, it is possible to recognize if the combination is correct or not, thereby it is possible to prevent from making a wrong combination. Also, since it is possible to recognize if the combination is correct or not on first sight, burden of workers to check can be reduced.

MODES FOR CARRYING OUT THE INVENTION

The functions and benefits of the present invention described above will be apparent from the following modes for carrying out the invention. Hereinafter, the present invention will be described based on the embodiments illustrated in the drawings. However, the invention is not limited to the embodiments. It should be noted that the drawings are sometimes shown transparent, exaggerated, or modified as needed in order to make the drawings easy to understand.

Figure 1A:
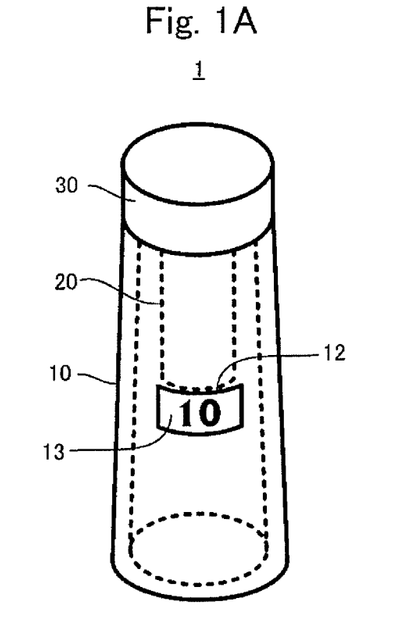
FIG. 1A is a perspective view of an implant fixture storage case 1 according to one embodiment.
Figure 1B:
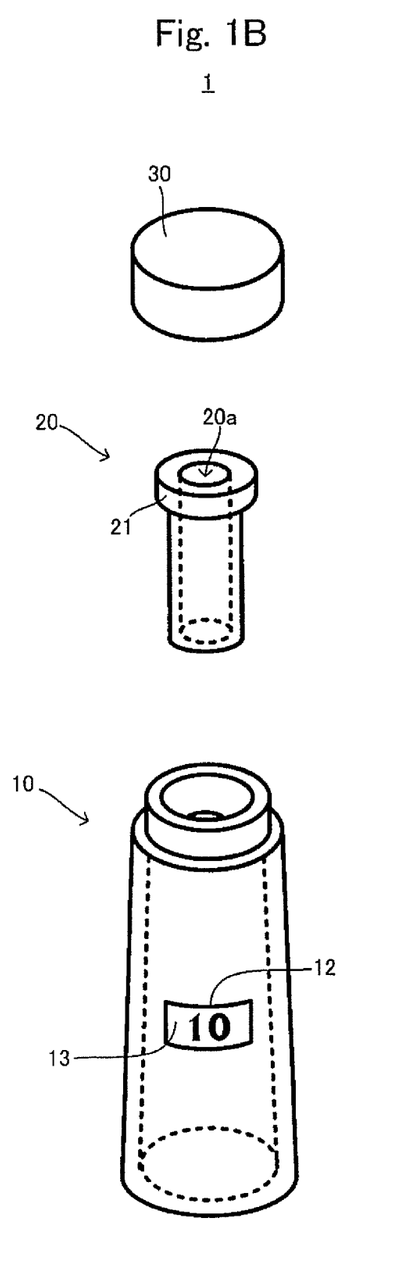
FIG. 1B is an exploded perspective view thereof.
Figure 2A:
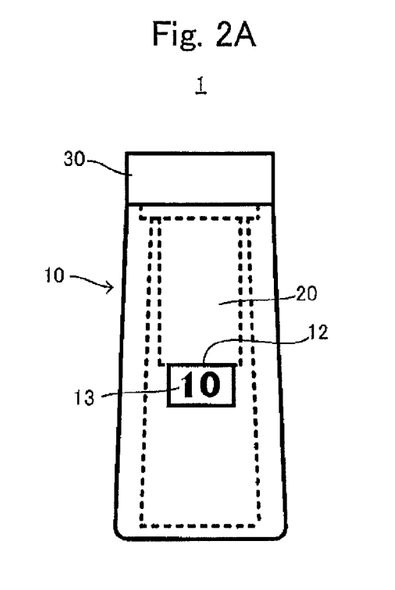
FIG. 2A is a front view of the implant fixture storage case 1 according to one embodiment.
Figure 2B:
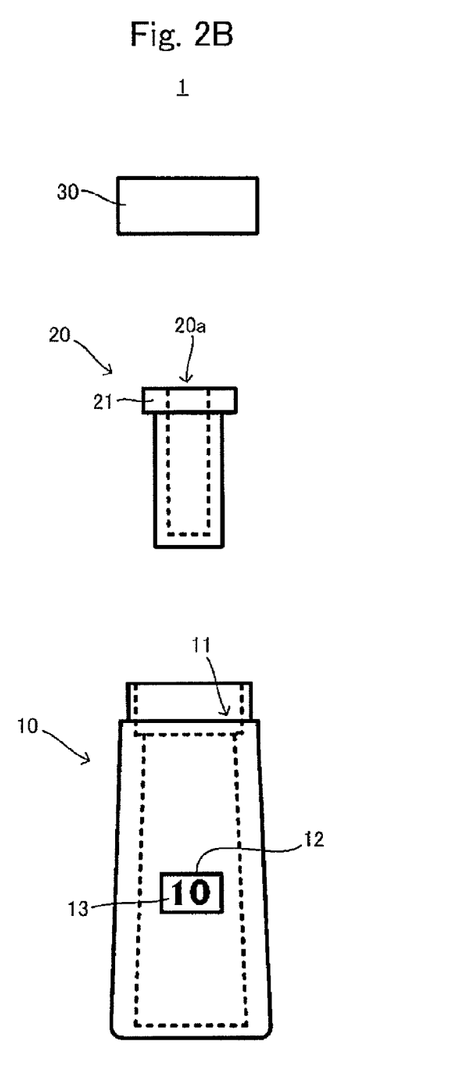
FIG. 2B is an exploded view thereof.
Figure 3:
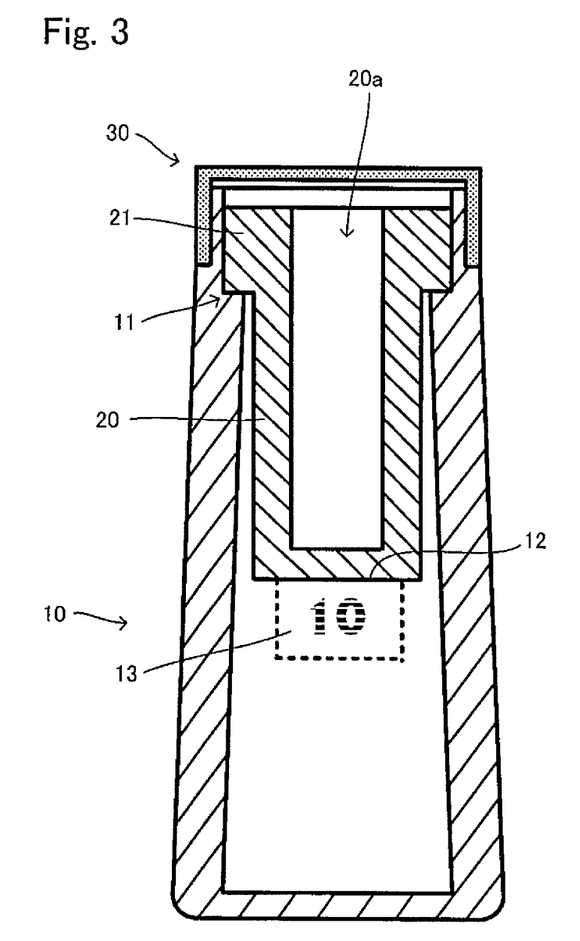
FIG. 3 is a cross-sectional view of the implant fixture storage case 1.

FIG. 1A is a view illustrating one embodiment, a perspective view of the implant fixture storage case 1, and FIG. 1B is an exploded perspective view thereof. FIG. 2A is a front view of the implant fixture storage case 1, and FIG. 2B is an exploded view thereof. FIG. 3 is a cross-sectional view of the implant fixture storage case 1, and FIG. 4 is an exploded view thereof.

The implant fixture storage case 1 is a case to store an implant fixture, and configured having a storage main body 10, an implant fixture holding member 20 to be inserted and held in the storage main body 10, and a cap 30 to close an opening end of the storage main body 10.

The storage main body 10 is a case having a cylindrical shape in which at least one end portion is open. The storage main body 10 is made of glass or plastic since it does not have direct contact with an implant fixture, and at least one part of the storage main body 10 is formed transparent so that the implant fixture holding member 20 stored inside is viewable. Also, the storage main body 10 can have a bottom on the other end portion.

Figure 4:
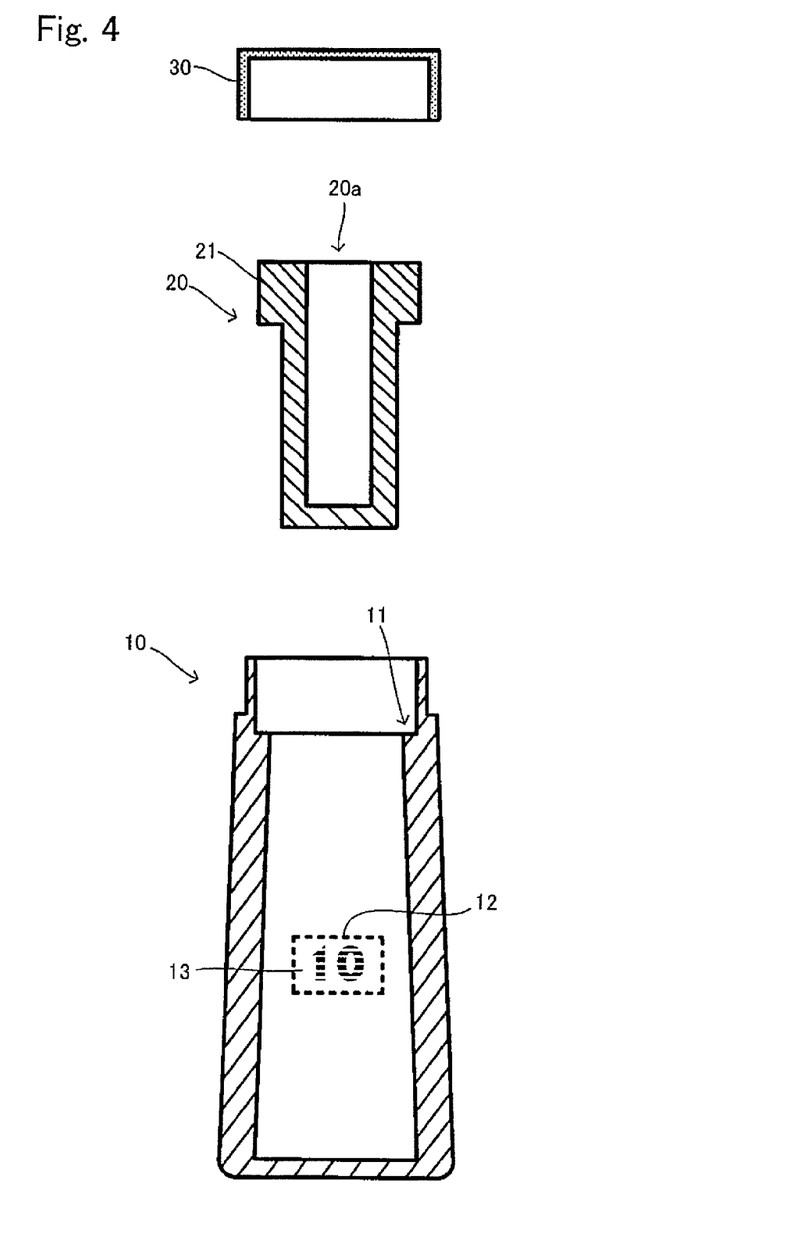
FIG. 4 is an exploded view of FIG. 3.

In the storage main body 10, as shown well in FIGS. 3 and 4, an outer periphery on an opening side thereof is slightly narrowed, and a screw to fit to the cap 30 is provided on a surface of the outer periphery. On the other hand, on a surface inside the storage main body 10, the storage main body 10 has a portion where a step 11 is formed such that the opening side is wider than the other side. As described later, the step 11 is configured such that an expanded portion 21 of the implant fixture holding member 20 is caught thereon.

Further, in the storage main body 10, a position display means 12 and a length display portion 13 are provided. The position display means 12 is provided based on the length of the implant fixture holding member 20. In this embodiment, as can be seen from FIG. 1 to FIG. 4, the position display means 12 is formed by one side of the length display portion 13 sectioned in a rectangle shape on the surface of the outer periphery of the storage main body 10. That is, this embodiment is configured such that the position display means 12 is also used as the length display portion 13. The position display means 12 of this embodiment is configured such that the position display means 12 and an end portion on a bottom side of the implant fixture holding member 20 are identical to each other when seen in a front view of the implant fixture storage case 1 (direction shown in FIG. 2 to FIG. 4).

The length display portion 13 is a portion on which a nominal length of the implant fixture to be stored is displayed with a number. That is, a value related to the length of the implant fixture to be stored is shown on the length display portion 13, which makes the length of the implant fixture being stored obvious. In this embodiment, the length display portion 13 is sectioned in a rectangle shape, and the value is displayed in the sectioned area. Examples in FIG. 1 to FIG. 4 each shows that an implant fixture having a nominal length of 10 mm is stored. Because of this, a length of the implant fixture being stored can be directly recognized.

The implant fixture holding member 20 is a member having a bottomed-cylindrical shape in which one side is open and the other side has a bottom. A storage space 20a is formed inside of the implant fixture holding member 20. An implant fixture is directly inserted to the storage space 20a. Also, on an opening side of the implant fixture holding member 20, an expanded portion 21 in which an outer periphery is expanded is provided.

A length in an axis direction of the cylindrical shape of the implant fixture holding member 20 (length in top and bottom direction of plane sheet of FIG. 2 to FIG. 4) is based on the nominal length of the implant fixture stored in the storage space 20a. Therefore, the implant fixture holding member 20 for holding an implant fixture that is large in nominal length becomes long, and an implant fixture holding member 20 for holding an implant fixture that is small in nominal length becomes short.

The implant fixture holding member 20 is made of titanium or titanium alloy.

The cap 30 is a so-called lid to close the end portion on the opening side of the storage main body 10, as can be seen from FIG. 1 to FIG. 4. Therefore, the cap 30 is a member having a bottomed-cylindrical shape in which one side is open and the other side is to be a bottom, and on a surface of an inner periphery, a screw to fit to the screw provided to the outer periphery on the opening side of the storage main body 10 as described above is provided. A material to configure the cap 30 is not particularly limited, and can be formed of plastic.

Structure members described above are combined as follows to be the implant fixture storage case 1 in which an implant fixture is stored. That is, an implant fixture is held inside of the storage space 20a of the implant fixture holding member 20. At this time, the implant fixture holding member 20 having a length that corresponds to a nominal length of the implant fixture to be stored is used.

The implant fixture holding member 20 in which an implant fixture is stored is held inside the cylindrical shape of the storage main body 10 as can be seen well from FIG. 3. At this time, the bottom of the implant fixture holding member 20 is to be on a side of the other end of the storage main body 10 (a bottom side when the storage case itself has a bottom). Therefore, the opening of the storage space 20a of the implant fixture holding member 20 and the opening of the storage main body 10 are open toward a same direction. The expanded portion 21 of the implant fixture holding member 20 is caught on the step 11 provided inside the storage main body 10, thereby the implant fixture holding member 20 is held by the storage main body 10.

The cap 30 closes the opening of the storage main body 10 and the opening of the storage space 20a of the implant fixture holding member 20 in a manner to cover them. At this time, the screw provided on the surface of the inner periphery of the cap 30 fits to the screw provided to the outer periphery of the end portion on the opening side of the storage main body 10, thereby the cap 30 and the storage main body 10 are connected.

In the implant fixture storage case 1, the storage main body 10 that forms entire external is formed of glass, plastic and the like, and what made of titanium or titanium alloy is limited to only the implant fixture holding member 20. Therefore, it is possible to reduce amount of titanium and titanium alloy to use.

Also, since lengths of the implant fixture holding members are changed in accordance with a nominal length of the implant fixture to be stored, the implant fixture holding members cannot be wastefully large in length, and from this viewpoint as well, it is possible to reduce amount of titanium and titanium alloy to use. Also, by changing the lengths, it is possible to inhibit forming a wasted space between the storage space and the implant fixture to be stored, to thereby enabling to prevent the implant fixture from moving widely in the implant fixture holding member when the implant fixture is carried and the like, thus enabling to prevent the implant fixture from being damaged.

As this embodiment, when the implant fixture holding member is formed in a cylindrical shape, it can be easily produced, and the cost can be reduced. Also, when the implant fixture holding member is formed in a cylindrical shape, since the implant fixture holding member is held in a manner to cover entire outer periphery of the implant fixture, it is difficult to be subjected to impact directly, then the shape is favorable from viewpoint of protection as well.

On the other hand, with regard to the cap according to this embodiment, as long as the cap has a function as a lid, a structure to hold an implant fixture is not especially needed. Therefore the cap has a simple shape and is easily produced.

Figure 5:
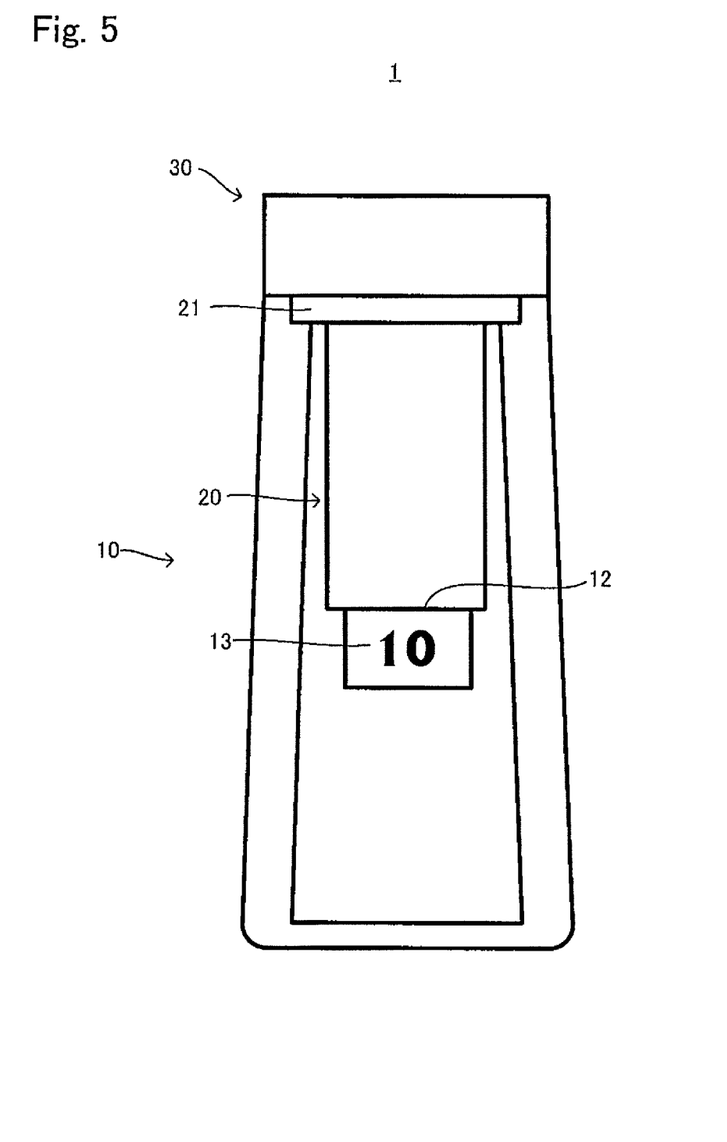
FIG. 5 is a front view of the implant fixture storage case 1.

In the implant fixture storage case 1 combined as above, the implant fixture holding member 20 having a length that corresponds to a nominal length of an implant fixture to be stored is used, and a position of the position display means 12 comprised to the storage main body 10 is determined based on the length of the implant fixture holding member 20. The implant fixture storage case 1 can be seen as follows. FIG. 5 shows a front view of the implant fixture storage case 1, seen from a direction in which the position display means 12 is at the front.

As can be seen from FIG. 5, in the implant fixture storage case 1, the storage main body 10 is transparent so that at least an end portion of the bottom side of the implant fixture holding member 20 is viewable, and configured such that the position display means 12 is also viewable at the same time. In this embodiment, the position display means 12 (in this embodiment, one side of the length display portion 13) and the end portion on the bottom side of the implant fixture holding member 20 are configured to be identical to each other seen from the front. This makes it possible to recognize combination of the value of the nominal length displayed on the length display portion 13 of the storage main body and the implant fixture holding member 20 that is actually stored, without any mistake. Because of this, when the implant fixture storage case 1 is assembled, or after assembled, mistake can be clearly seen at the check and so on, thereby it is possible to provide an appropriate implant fixture storage case 1. Also, since the mistake can be clearly seen, it is possible to reduce burden of the person to check.

Figures 6A, 6B:
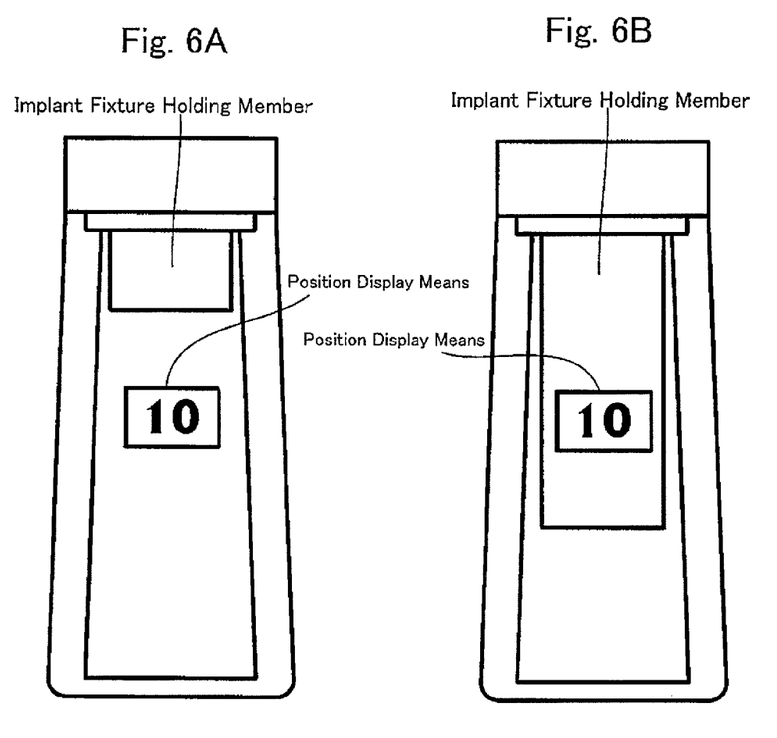
FIG. 6A is a wrong combination example in which a short implant fixture holding member is combined.
FIG. 6B is a wrong combination example in which a long implant fixture holding member is combined.

FIG. 6 shows examples in which there were mistakes in combinations. FIG. 6A shows an example in which a short implant fixture holding member is combined, and FIG. 6B shows, to the contrary, an example in which a long implant fixture holding member is combined. As can be seen from FIGS. 6A and 6B, since each implant fixture holding member differs to one another in length, in accordance with an implant fixture to be stored, if the implant fixture holding member is paired with a wrong storage main body, the implant fixture holding member and the position display means do not have the predetermined positional relationship. Because of this, it is possible to recognize on first sight that a wrong implant fixture holding member is paired with the storage main body.

Figure 7A:
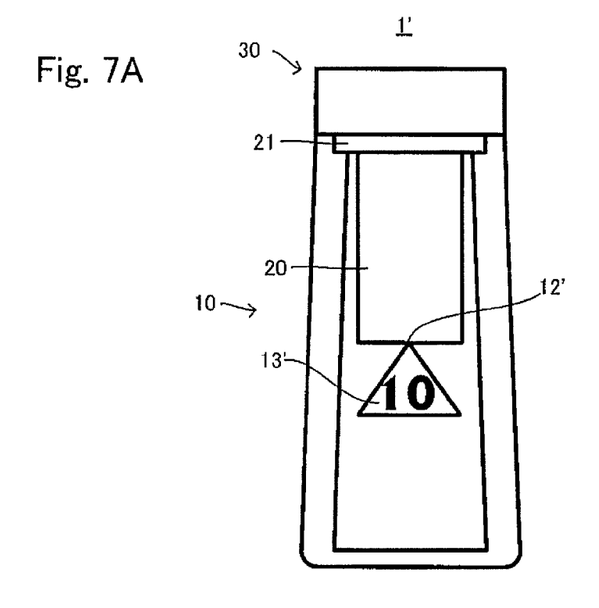
FIG. 7A is a front view of an implant fixture storage case 1'.

FIG. 7 shows a modified example. FIG. 7A is a view illustrating an implant fixture storage case 1'. In the implant fixture storage case 1', a length display portion 13' is sectioned in a triangle shape, and a value based on a length of an implant fixture to be stored is displayed thereon. On the other hand, a position display means 12' is formed by one apex of the length display portion 13'. In this example as well, the position display means 12' is also used for the length display portion 13'.

Figure 7B:
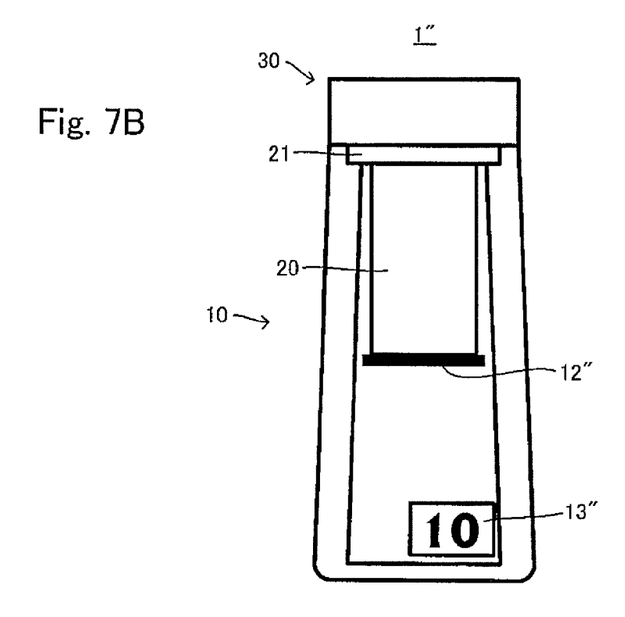
FIG. 7B is a front view of an implant fixture storage case 1"

FIG. 7B is a view illustrating an implant fixture storage case 1". The implant fixture storage case 1" is an example in which a position display means 12" and a length display portion 13" are provided separately. The position display means 12" is positioned as the examples described above, and in this example, formed by one line. On the other hand, the length display portion 13" is provided to the storage main body 10 having no relationship with the position display means 12".

The implant fixture storage cases 1' and 1" according to modified examples also exert same effect as above.

Figure 8:
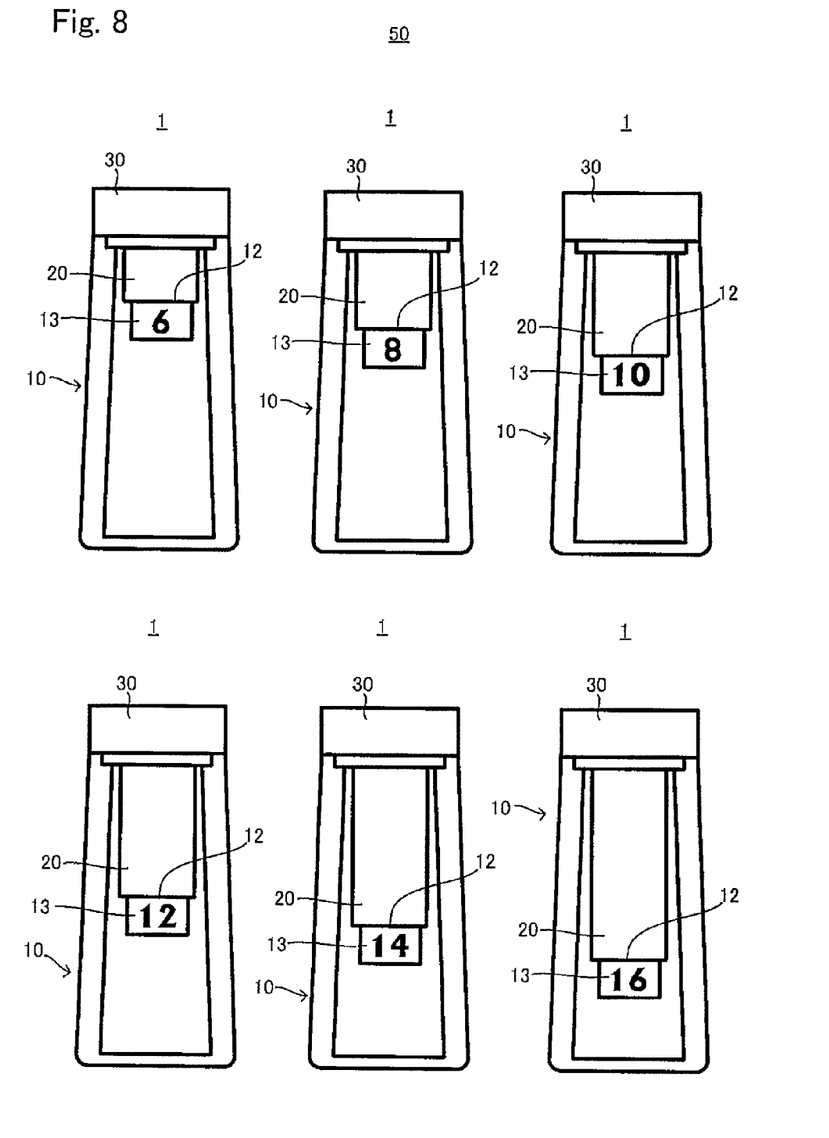
FIG. 8 is a view illustrating an implant fixture storage case set 50.

In FIG. 8, an example in which a plurality of the implant fixture storage cases 1 described above are combined to be one implant fixture storage case set 50. In this example, six implant fixture storage cases 1 respectively comprising implant fixture holding members 20 in which implant fixtures having six different nominal lengths (6 mm, 8 mm, 10 mm, 12 mm, 14 mm, 16 mm) are stored are gathered to configure the implant fixture storage case set 50.

As can be seen from FIG. 8, each implant fixture holding member 20 differs in length corresponding to the nominal length of the implant fixture. Because of this, when implant fixture holding means having different lengths are held in storage main bodies, positions of bottoms of the storage main bodies are different from one another. In the storage main body 10, a position of the position display means 12 is configured such that the end portion on the bottom side of the implant fixture holding member 20 is identical to the position display means 12 when seen from the front.

As shown the above, when a plurality of implant fixtures having different nominal lengths are provided as a set, mistake in combination tends to occur more often. However, according to the present invention, it is possible to recognize the mistake in combination at first sight, thereby it is possible to prevent such a mistake.

Here, the implant fixture storage case set 50 including six kinds of implant fixture storage cases 1 has been described, but the present invention is not limited to this, and when a set is provided, at least two kinds can be combined. Also, the plurality of the implant fixture storage case 1 can be combined to configure a set such that some or all of the implant fixture storage cases 1 are same, or different.

DESCRIPTION OF THE REFERENCE NUMERALS 1 implant fixture storage case
10 storage main body
12 position display means
13 length display portion
20 implant fixture holding member
30 cap

The invention claimed is:

1. An implant fixture storage case comprising:
 an implant fixture holding member for holding an implant fixture and which has a length based on a length of the implant fixture to be held; and
 a storage main body on which a value related to the length of the implant fixture is displayed, and which holds the implant fixture holding member thereinside and has at least one part being transparent, and
 a position display means provided to the storage main body based on a position of an end portion of the implant fixture holding member,
 wherein the end portion of the implant fixture holding member and the position display means are viewable at the same time.

2. The implant fixture storage case according to claim 1, wherein a portion on which the value related to the length of the implant fixture is displayed is also used for the position display means.

3. The implant fixture storage case according to claim 2, wherein the portion on which the value related to the length of the implant fixture is displayed is a portion sectioned in a rectangle shape, and one side of the rectangle shape functions as the position display means.

4. The implant fixture storage case according to claim 1, wherein the implant fixture holding member is formed in a cylindrical shape having a bottom on one side.

5. An implant fixture storage case set comprising a plurality of the implant fixture storage case according to claim 1.

6. The implant fixture storage case set according to claim 5, wherein the plurality of the implant fixture storage cases have at least two kinds of implant fixture holding members having different lengths from each other.

* * * * *